United States Patent [19]

Vesterberg

[11] 4,337,131

[45] Jun. 29, 1982

[54] PROCESS FOR ELECTROPHORESIS

[75] Inventor: Olof Vesterberg, Saltsjö-Duvnäs, Sweden

[73] Assignee: C. Desaga GmbH Nachf. Erich Fecht, Heidelberg, Fed. Rep. of Germany

[21] Appl. No.: 94,308

[22] Filed: Nov. 13, 1979

[30] Foreign Application Priority Data

Nov. 13, 1978 [SE] Sweden .............................. 7811720
Nov. 2, 1979 [DE] Fed. Rep. of Germany ....... 2944127

[51] Int. Cl.³ ...................... B01D 57/02; G01N 21/26
[52] U.S. Cl. ............................. 204/180 G; 204/299 R
[58] Field of Search ....................... 204/180 G, 299 R

[56] References Cited

U.S. PATENT DOCUMENTS 3,932,265  1/1976  Hoefer .................................. 204/299
4,200,508  4/1980  Hirai et al. ...................... 204/180 G Primary Examiner—F. Edmundson
Attorney, Agent, or Firm—Wenderoth, Lind & Ponack

[57] ABSTRACT

The invention concerns an electrophoretic process for the investigation, analysis, and/or production, especially immunoelectrophoretic, of chemical substances, in which the substances to be investigated or the starting materials for the substances are transported in aqueous solution in a gel carrier medium. For inhibiting or stabilizing convective transport under the action of an electric field, the aqueous solution contains reagents which form precipitates with the substances to be determined quantitatively. Due to electrophoretic transport in the aqueous phase of the carrier medium these reagents result in the production of precipitation over a migration distance which is proportional to the amount of the substances being determined.

5 Claims, 4 Drawing Figures

PROCESS FOR ELECTROPHORESIS

In the quantitative determination of substances such as proteins, for example, one type of immunoelectrophoresis used, for example, is called "rocket electrophoresis" (see Lawrell, C. B., Anal. Biochem. 1966, 15:45 ff). In this method a layer of a water-containing agarous gel about 1 mm thick is applied to the top side of a horizontally disposed glass plate, and in this gel are antibodies against antigens which are in fact the substances to be determined. The sample solutions to be analyzed, which contain the antigens, are placed in small round indentations which are previously cut out along one of the edges of the gel. Along this edge a liquid contact is effected with a vessel containing an aqueous buffer solution and furnished with a cathode electrode, said contact being effected with the aid of a wick-like connecting strip which, for example, is made of paper. The opposite edge of the layer of agarous gel is analogously brought into contact with a buffer solution in an anode vessel. While the glass plate lies horizontal on a cooled surface, the electrophoresis is conducted such that the antigens are transported into the agarous gel, in the direction of the anode. During this process the antigens react with the antibodies. Precipitates result which, viewed from above, resemble a rocket cone, with the vertex in the direction of the anode. The area bounded by the envelope of the precipitate and a tangent through the nearest part of the round indentation is, at least over a definite region, directly proportional to the amount of the antigen. An analogous proportionality is also found with respect to the maximum height (length) of the precipitate area region. Hereby not only antigens may be determined but also substances having a specific affinity to another substance and with which (determined substances) precipitates can be formed. Thus, for example, protein A from staphylococci can form precipitates with certain immunoglobulins, and lectins can form precipitates with proteins containing certain polysaccharides. These processes are called "affino-electrophoreses", and are carried out by a technique analogous to that for "rocket electrophoreses". One disadvantage of "rocket"-type electrophoreses is that a large portion of the reactive agents in the gel are not used. Another disadvantage is that very low protein concentrations cannot be determined with "rocket electrophoresis", even in combination with the protein stain method. Protein concentrations of about 5 mg per liter or higher can be determined, but only under very favorable conditions. Although this sensitivity is relatively good, currently there is a need to determine lower protein concentrations. A further disadvantage of "rocket electrophoresis" is the difficulty of accommodating a large enough volume of sample liquid in the indentations to achieve the desired sensitivity. A still further disadvantage is the amount of time required for the "rocket" method. In many cases the electrophoresis must be carried out over many hours, e.g. 12 hours or overnight; this is partly a function of the ability to remove heat with a cooler positioned under the glass plate. Heat removal is too ineffective for one to be able to increase the current to the desired degree so as to produce a significant shortening of the duration of the electrophoresis. When wick-like contacting means are employed, disadvantages also arise involving significant field losses and heat production. Such wick-like contacting means also contribute to contamination by microorganisms, proteins and the like.

The problem of the present invention is to devise an electrophoretic process of the initially abovedescribed type which is free of the disadvantages of the known processes, and which process, in particular, enables using larger amounts of sample liquid, in order to increase sensitivity, and enables the reagents employed to react under more favorable field conditions.

This problem is solved according to the invention by carrying out the electrophoretic transport in a carrier medium which is in the form of a thin layer held between at least two plate-like or film-like elements which are moveable with respect to each other, such that the opposite ends of the carrier medium are in direct contact with buffer solution contained in respective electrode containers associated with each of the ends, and such that after the electrophoretic transport one of the side surfaces of the carrier medium in the form of a thin layer is exposed, by the removal of at least one of the plate-like or film-like elements.

This new electrophoretic process is suitable for the quantitative or semiquantitative determination of substances and for immunoelectrophoretic investigations and analyses in a carrier medium in a comparatively very short process time, for example down to as little as one sixth the time needed for "rocket" electrophoresis. The inventive process is thus very valuable for use in, for example, hospitals, where a speedy result is desirable or necessary. The inventive process affords greater sensitivity, especially via the ability to process larger sample sizes, for example more than 10 times the size accommodatable in "rocket" electrophoresis. By using a carrier medium which can be substantially exposed after carrying out the electrophoresis, subsequent operations such as staining or the like can be performed quickly and effectively. Because the carrier medium is in direct contact with the buffer solutions, the disadvantages connected with the use of wick-like contact means with regard to the deleterious effect on the electric field and with regard to contamination are precluded.

Preferably the electrophoretic transport is carried out in a vertical carrier medium in the form of a thin layer which is in direct contact with one of the buffer solutions near its (the layer's) upper edge and another near its lower edge.

If, according to a further refinement of the invention, the electrophoretic transport is carried out in a carrier medium in the form of a thin layer which is divided into multiple essentially parallel strips, the electrophoresis can be performed for multiple samples, corresponding to the number of strips. Despite the division into strips, the exposure of the carrier medium after the electrophoresis can be effected in simple fashion.

According to a still further refinement of the invention the electrophoretic transport is carried out in a carrier medium which is in the form of a thin layer which is divided into multiple essentially parallel strips which are in contact or connection with each other over a narrow stretch, preferably near the end opposite to the one on which the sample is applied. This enables a common direct contact to be accomplished in simple fashion between the carrier medium divided into strips and the second buffer solution.

If the strips of the carrier medium for the electrophoretic transport are each held in a channel-shaped compartment, and if the substances to be analyzed are applied to the respective strips from a section of the respective compartment, which section extends outwardly from the end face of the strip, then along with favorable geometry for carrying out the electrophoresis, and along with simple exposability of the strips of carrier material, a relatively large sample volume can be used.

If the carrier medium contains a reagent which promotes precipitation of the substance to be analyzed and-or opposes electro-endosmosis—a reagent such as polyethylene glycol, the effectiveness of the inventive process can be still further improved.

Likewise if the substances to be analyzed are employed in a sample solution which has a different ionic composition and-or ionic concentration from that (or those) in the water solution of the carrier medium.

The invention also concerns a device for conducting the above-described process, which device comprises channels containing the carrier medium, e.g. a gel, the opposite ends of which channels are in contact with electrode vessels containing buffer solution and connected to opposite poles of a direct current source; and which device is distinguished by a support plate which has elongated, essentially parallel troughs, slots, grooves or the like, which are designed to hold the strips of carrier medium and which are sealable by applying at least one plate-like or film- or foil-like element to the corresponding flat side of the support plate at its exposed longitudinal side, whereby if necessary end regions at the top and bottom may be left still exposed. With such a device the inventive process can be carried out with a simple arrangement in an effective manner, whereby in particular the strips of carrier medium are easily and quickly accessible after the electrophoresis.

Under a certain refinement of the inventive device the troughs, slots, grooves or the like are in communication with each other, preferably in the neighborhood of the end opposite the sample-application end, via a trough, channel, groove or the like which runs transversely.

One specific embodiment of the inventive device comprises a support plate which has open troughs facing a flat side, with which flat side the support plate may be applied against a front plate of one of the electrode vessels, whereby the troughs reach beyond the threshold of a recess provided at the top edge of the front plate; and wherein the support plate has a slit for connecting with the other electrode vessel, said slit being located in the region of the transverse trough which connects the (parallel) troughs and running essentially over the length of the transverse trough, and said slit being coverable on the side turned away from the support plate.

It is also possible for the support plate to have open slots separated by a lathing configuration and facing both flat sides of the support plate; whereby the support plate may be applied, with one of its flat sides, against a front plate of one of the electrode vessels such that the slots reach beyond the threshold of a recess provided at the top edge of the front plate; and such that the slots are in mutual communication via a transverse channel formed within the lathing configuration; and further such that a bracket plate may be applied against the outer flat surface of the support plate, said bracket plate having a transverse slit in the region of the transverse channel, for connecting with the second electrode vessel, which slit if necessary is adjustable so as to basically line up with the channel.

With the earlier-mentioned first embodiment there may also be a bracket plate which may be applied to the outer flat side of the support plate, which bracket plate has a slit coordinated with the bottom end of the trough, which slit is adjustable so as to basically line up with the slit in the support plate.

In a third embodiment of the inventive device it is provided that the support plate may be in the form of a wall of one of the electrode vessels, which on one surface has grooves separated by ribs, which grooves all reach at their upper end a threshold of a recess provided at the top edge of the wall; and it is provided that the grooves are coverable by a plate-, sheet-, film-, or foil-like element which may be applied to the face having the grooves, if necessary as far as a slot in the region of a transverse groove which connects the aforesaid grooves on the wall.

Accordingly, a device may be used for the inventive process with the device-parts made of a light-transmitting material, such as glass, polyethylene, polystyrene, or polymethacrylate. The device has basically two electrode vessels in which the electrodes, made of platinum, for example, are disposed, and has basically flat elements in the nature of walls, plates, sheets, films, or foils for confining the carrier medium which is the site of the electrophoretic transport of the substances to be analyzed. The carrier medium may be a gel of, e.g., agar, agarose, polyacrylamide, or cellulose acetate, and may particularly contain water-soluble buffer substances as well as added antibodies and analogous substances which specifically react with the components to be determined, forming precipitates in the carrier medium. The carrier medium is thus confined as a layer between two disassemblable elements with flat configurations between which separate compartments for accommodating the carrier medium in strips can be provided. These compartments may have circular, oval, or rectangular cross section. Elongated carrier medium strips of a, e.g., gel nature are arranged in parallel in these compartments, with dimensions, e.g., 3 mm wide, 1.5 mm deep, and 60 mm long. The flattish boundaries of the carrier medium strips need not be strictly flat, but for example they may be curved, particularly with curves matching the wall of the given electrode vessel itself. The elongated compartments provided between the flat boundaries, for accommodating the carrier medium, are vertically filled, e.g., only up to half their height with the carrier medium. The individual sample solutions can then be inserted on top from above, using capillary tubes. Due to the fact that the flattish boundaries of the layerlike carrier medium have suitable recesses at the top and bottom end, direct contact between the carrier medium and the buffer solutions can be effected easily and effectively. By employing isotachophoretic /sic/ principles, or at least taking into account the conductivity and-or pH of non-continuous buffer systems it is also possible to concentrate the substances to be determined, during their electrophoretic transport from top to bottom.

At least one of the flat elements in the nature of walls, plates, sheets, films, or foils which confine the carrier medium is made of transparent material such as glass or plastic, particularly polystyrene, polyethylene, polyvinyl chloride, polycarbonate, or polyester, and is preferably of thin material under 1 mm thick, in order to increase the cooling effect. The cover or boundary of the layerlike carrier medium is in each instance devised such that each sample or test compartment is connected to the two buffer solutions used for electrophoresis at each end. The contact here is direct, producing good liquid contact with the buffer solutions in the electrode vessels, preferably at the upper and at the lower end of the carrier medium, so that contacts using wick-like contacting means are not needed.

During electrophoresis the substances to be determined are transported from their respective sample compartments into the carrier medium. Here they react with substances previously distributed in the carrier medium which have a high specific affinity for the sample substances being analyzed for. Such a reaction pair may involve an antigen and an antibody, or protein lectins and receptor-specific proteins, in analogy with affino-electrophoresis. In the process the precipitates are formed in zones which can be made visible by protein staining, for example (see, for example, Krantz, Th. et al. 1974. Z. Klien. Chem. Klin. Biochem. 12:124), or simply by denaturing. The more of the sample substance which is to be determined which is present, the longer the segment will be over which the precipitates are formed in the carrier medium. There is nearly direct proportionality between this path length and the sample length.

Good conditions prevail for the removal of the Joule heat generated during the electrophoresis in the carrier medium; these good conditions are due to the thin wall of at least one of the confining walls, and the good liquid contact between this wall and the buffer solution. The heat transferred to the buffer solution may be removed therefrom in simple fashion, by a heat exchanger.

As a result of this improved cooling system and the elimination of wick-like contact means, significantly higher electric field strengths can be attained in the carrier medium than heretofore, and accordingly the time required for carrying out the electrophoresis can be appreciably reduced.

Since according to the invention the layerlike carrier medium is enclosed between two walls which are disassemblable with respect to each other, relatively large amounts of sample solutions can be charged, with good accessibility of the carrier medium after the electrophoresis.

Additional features, advantages, and application possibilities of the present invention will be seen from the following description of example embodiments with the aid of the drawings attached hereto. In this connection, the subject of the present invention includes all features which are described and-or which are disclosed in the drawings, either as presented or in any useful combination, regardless of whether they are summarized or referenced in the claims.

Figure 1:
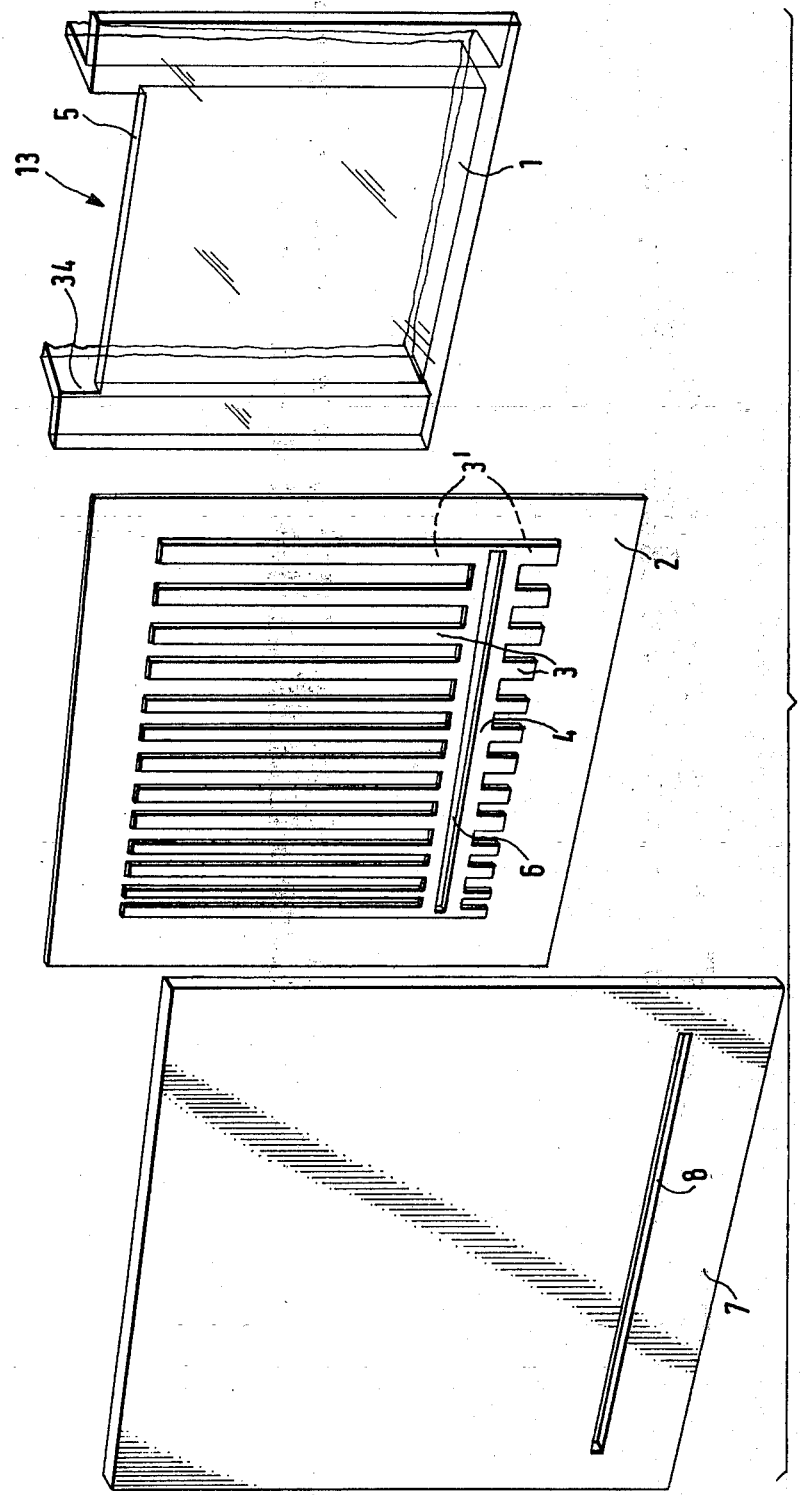
FIG. 1 shows schematically, pulled apart, and partly broken away, the bracket plate, the support plate furnished with troughs for accommodating the carrier medium, and the front plate of an electrode container, of a device embodying the invention.

FIG. 1 shows the front plate 1 of an (inner) electrode vessel 13 (see also FIG. 3), which front plate is made of glass, for example. A support plate 2 which is made of relatively thin plastic material, e.g. polystyrene or polyvinyl chloride, has ribs 3 protruding from one surface of support plate 2, which ribs on the back side form elongated channel-shaped vertical troughs 3'. The troughs 3' are closed on the front side by the material of the support plate forming the ribs 3, and may also be covered on the back side by applying the support plate 2 against the outer surface of the front plate 1, to form closed, tube-like channels. The troughs 3' may alternatively be closed on the back side during the filling of their space with the carrier medium and during storage (with carrier medium inside) by applying a thin sheet, film, or foil. The support plate 2 can be fabricated in simple fashion by vacuum forming of a thin sheet of material. In the bottom region the troughs 3' are interconnected by a horizontal trough 4 which forms a horizontal closed tube when support plate 2 is pressed against front plate 1, which tube connects to the vertical tubes formed by troughs 3'. Bracket plate 7 can be applied and pressed against support plate 2 from the outer side. Support plate 2 and bracket plate 7 may be affixed to the front plate by clamps, for example.

The clamps (not shown) may be applied at the sides and the bottom edge of front plate 1, for example. In order to obtain a tight seal at the contact surfaces between support plate 2 and, on one side, front plate 1, and on the other side bracket plate 7, it may be advantageous to lubricate the plates in their edge regions before bringing them together, or to apply a non-permanent adhesive which allows later separation. When the carrier medium solution, for example a gel, is being charged into the vertical tubes formed by troughs 3', horizontal trough 4 serves as a connecting conduit, to enable easy filling of all the tubes formed from vertical troughs 3' (formed, for example, by applying a sheet, film, or foil), up to a desired height in a single filling operation. In this way multiple, parallel, vertical strips of the carrier medium are generated in troughs 3' of support plate 2. Above each carrier medium strip in the associated trough 3' there is an upper compartment which is kept open for charging the sample solution by means of a capillary. Troughs 3' are of such a length that when support plate 2 is mounted flush they are exposed to electrode vessel 13 in the region of an upper recess 34 in the front plate 1, which recess is bounded on the bottom by sill 5. In this region the strip-shaped carrier medium can be in direct contact with the buffer solution present in the inner electrode vessel 13, which solution is at a level above that of sill 5. In accordance with this the other walls of electrode vessel 13 extend higher than front plate 1 in the region of the upper edge recess 34, as seen from FIGS. 1 and 3. At the bottom end of the gel-like carrier medium contained in the troughs 3' and 4, direct contact with a buffer solution contained in the outer electrode vessel 14 (FIG. 3) is effected via a transverse slit 6 in the support plate 2 in the region of the horizontal trough 4. When the carrier medium solution is being charged into troughs 3' and 4, slit 6 is covered by bracket plate 7, which rests against ribs 3 and the rib corresponding to trough 4. Bracket plate 7 has a slit 8 corresponding to slit 6, and by vertical shifting of bracket plate 7 slit 8 can be moved into a position which lines up with slit 6; this position is maintained during the electrophoresis. Before the start of the electrophoresis the unit comprising the inner electrode vessel 13, support plate 2, and Bracket plate 7 according to FIG. 3 is inserted in outer electrode 14 which is full of buffer solution.

The electrophoretic transport of the substances to be determined proceeds downward from the top compartments in troughs 3', so that said substances come into contact with reagents which have been previously introduced into the carrier medium in water solution, and said substances form precipitates with said reagents. After the electrophoresis has been carried out, easy access to the carrier medium strips may be had by removing support plate 2 with bracket plate 7 from front plate 1. By dumping the carrier medium strips onto a glass plate they can be dried and-or the precipitates in them can be stained.

Figure 2:
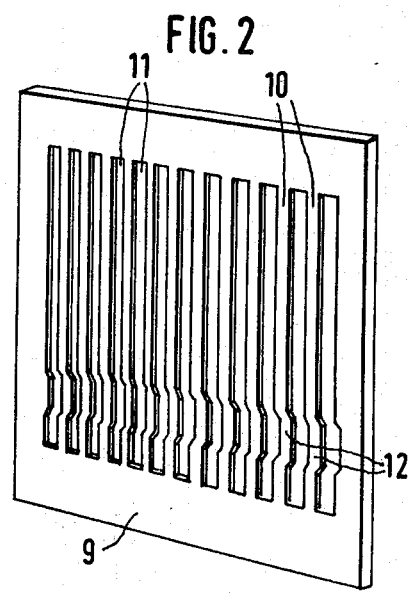
FIG. 2 is a schematic perspective view of a different design of a support plate for accommodating the carrier medium in strips.

FIG. 2 depicts a support plate 9, which also may be made of plastic, for example polymethacrylate, polystyrene, or polyvinyl chloride. Vertical slots 11 are formed in the support plate 9 by means of a vertical lathing configuration 10. The width of each of the multiple laths 10 is between 1 and 5 mm. In the bottom region of lathing configuration 10 a horizontal channel 12 is formed from indentations in the lathing 10. When support plate 9 is placed with its far flat side against front plate 1 and the front flat side of support plate 9 is covered by bracket plate 7, slots 11, which are now covered on both sides, form (as with other configurations described supra) vertical channels for accommodating the carrier medium in the form of strips which further are mutually connected via horizontal channel 12. The charging of the carrier medium is accomplished as described in connection with FIG. 1, i.e., with horizontal slit 8 being displaced with respect to horizontal channel 12. During the conducting of the electrophoresis the bracket plate can be shifted vertically so that slit 8 is in coincidence with channel 12, thus producing the connection with the buffer solution in the outer electrode vessel 14.

Figure 3:
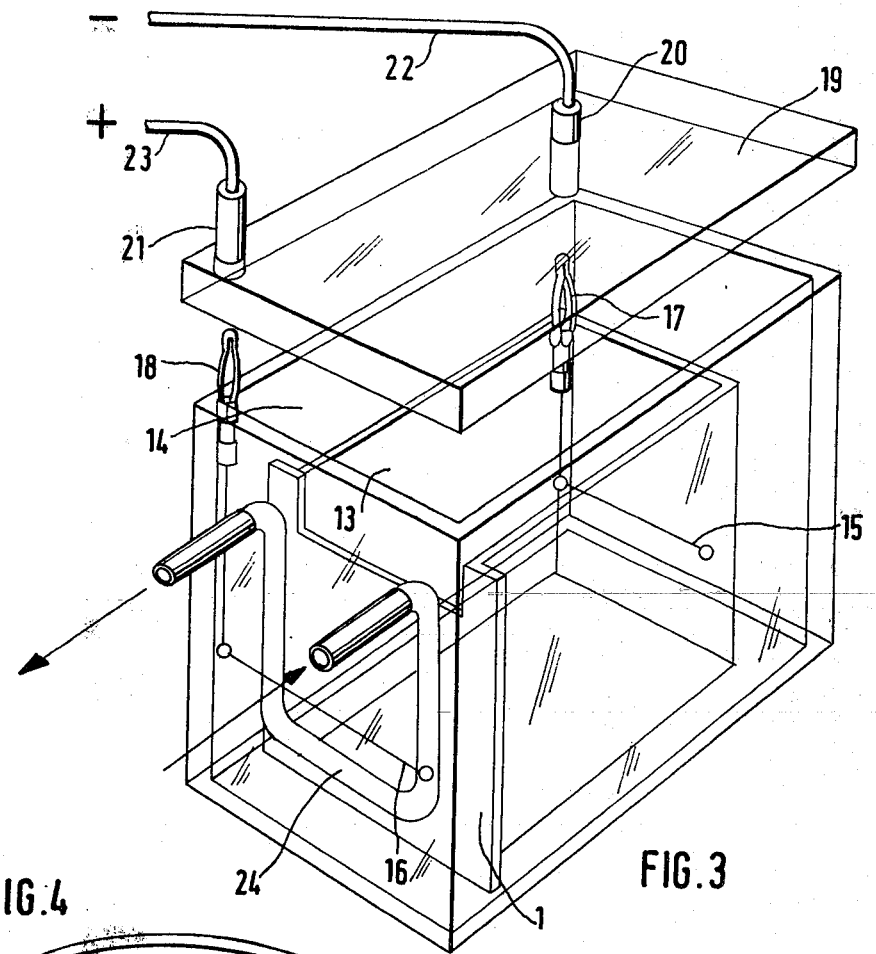
FIG. 3 is a schematic perspective view of an embodiment of the inventive device for carrying out the inventive electrophoretic process.

FIG. 3 shows the inner electrode container 13, bearing front plate 1, standing inside outer electrode container 14. Containers 13 and 14 can be fabricated from glass or plastic. They have electrodes 15 and 16, respectively, which may be made of platinum wire, for example, and are connected to banana plugs 17 and 18 on the walls of electrode vessels 13 and 14. There are counterpart sockets 20 and 21 on cover 19, from which there are leads 22 and 23 which extend to the two poles of a direct current source. When cover 19 is put in place on outer electrode vessel 14 an electrical contact is established between banana plugs 17 and 18 and the sockets 20 and 21, respectively. The Joule heat which is absorbed during the electrophoresis by the buffer solutions in vessels 13 and 14 is removed by means of a cooling tube 24 through which a cooling fluid flows in the direction shown by the arrows.

Figure 4:
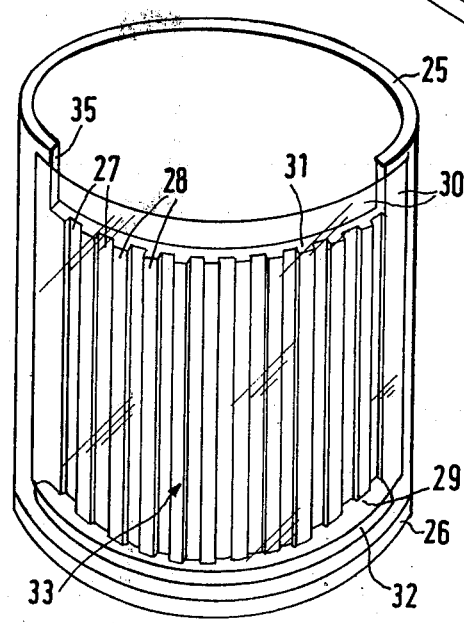
FIG. 4 is a schematic perspective view of a further refinement of the inventive device in which the support plate which holds the carrier medium in grooves is in the form of a wall of the inner buffer electrode vessel.

FIG. 4 depicts an embodiment of an inner electrode vessel 25 with a circular cross section and a bottom 26 which is mounted water-tight. A recess 35 extends over a certain wall region of electrode vessel 25 at the top edge. This recess is bounded by a bottom sill 31 with function the same as that of sill 5. Separated grooves 27 are provided in the outer surface of the vessel wall over the width of recess 35. These are separated by parallel vertical ribs 28. A support plate according to the invention results, which is intended to hold a carrier medium in the form of strips. Grooves 27 are interconnected by a horizontal transverse groove 29. Each groove 27 on its top end reaches sill 31. Transverse groove 29 and vertical grooves 27 may be jointly covered on the outside by, e.g., a transparent plastic sheet or film 30 which extends up over sill 31. In this way a system of vertical channels is formed by grooves 27 covered on the outside, which channels are interconnected by horizontal transverse groove 29 and open at their top end into inner electrode vessel 25. The channels may be filled with gel-type carrier medium solution, e.g. derived from agarose, up to the desired height. When the solution has, e.g., solidified to a gel, using a knife a small strip can be cut from sheet or film 30 in the region of transverse groove 29, so that after the inner electrode vessel 25 with sheet or film 30 is inserted in an outer electrode vessel corresponding to electrode vessel 14 the carrier medium in the form of strips is in direct contact at the bottom end with the buffer solution in the outer electrode vessel. Inner electrode vessel 25 is filled with buffer solution to a level above sill 31 so that the carrier medium in the form of strips is in direct contact at the top end with this buffer solution. The compartments in the grooves 27 above the carrier medium can then be filled with samples, as described in connection with FIG. 1.

In the following an example of a process according to the invention is described in more detail:

Ten microliters of a canine antihuman transferrin serum (from DAKO Immunoglobuline, of Copenhagen) was added to 10 ml of a 1% aqueous solution of agarose in 0.04 M water solution with pH 8.6, containing barbituric acid sodium salt and 4% polyethylene glycol and having a temperature of 55° C. After the tubes of a device according to FIG. 1 were charged with this solution, the gel solution reached up to around 3 cm below sill 5 of recess 34 in the front plate 1 of electrode vessel 13. After 20 min electrode vessels 13 and 14 were filled with buffer solution. To each sample compartment above the gel there was introduced 20 μl normal human serum in dilutions between 1:500 and 1:1600 in the abovementioned buffer solution but additionally containing 8% sucrose; the set of dilutions was at equal intervals of 100 in the denominator. Next a potential of 110 V was applied to electrodes 15 and 16 from a direct current source. After 2 hr the current was switched off and the device was disassembled. The gel strips were placed on a glass plate and air-dried. They were then immersed for 60 min in a protein stain solution containing 0.5% Coomassie Brilliant Blue R 250 (a sodium anoxynaphthonate dyestuff from ICI, of Manchester, England), 45% ethanol, 45% water, and 10% acetic acid. Then the excess stain was washed away with more of the above solution but without the dyestuff. In each gel strip the migration distance from the top, sample-application edge of the gel to the point of maximum migration of the precipitate was measured. This distance was proportional to the amount of the transferrin. In typical cases a regression coefficient of 0.97 was determined. This experiment showed that the inventive process is well suited for quantitative determination of substances.

Variations of the example procedure presented are readily possible. In particular, the support plate having been filled with gel may be covered on all sides and stored for several days. It may also be advantageous to keep the sample in an agarose solution with concentration of around 0.05 to 0.2% prior to introduction into the inventive device. This counteracts convective interferences and takes the place of the addition of sucrose and corresponding agents such as those named in the above examples.

List of Figure Labels

1: Front plate
2: Support plate
3: Ribs
3': Vertical troughs
4: Horizontal troughs
5: Sill
6: Slit
7: Bracket plate
8: Slit
9: Support plate
10: Lathing
11: Slots
12: Horizontal channel
13: Inner electrode vessel
14: Outer electrode vessel
15: Electrode
16: Electrode
17: Plug
18: Plug
19: Cover
20: Plug socket
21: Plug socket
22: Electrical lead
23: Electrical lead
24: Cooling tube
25: Inner electrode vessel
26: Bottom
27: Grooves
28: Ribs
29: Transverse groove
30: Sheet or film
31: Sill
32: Slot
33: Support plate
34: Recess
35: Recess

I claim:

1. In an electrophoretic process for the investigation, analysis, and/or production of chemical substances, in which the substances to be investigated or the starting materials for the substances to be produced are transported in aqueous solution in a gel carrier medium for inhibiting or stabilizing convective transport under the action of an electric field wherein the aqueous solution contains reagents which form precipitates with the substances to be quantitatively determined, and, due to electrophoretic transport in the aqueous phase of the carrier medium, these reagents result in the production of precipitation over a migration distance which is proportional in length to the amount of the substances being determined; and in which process the electrophoretic transport is carried out in a vertical carrier medium which is in the form of a thin layer held between at least two plate-like or film-like elements which are moveable with respect to each other, such that the opposite ends of the carrier medium are in direct contact with buffer solution contained in respective electrode containers associated with each of the ends, and such that after the electrophoretic transport one of the side surfaces of the carrier medium, which medium is in the form of a thin layer, is exposed by the removal of at least one of the plate-like or film-like elements, the improvement wherein the electrophoretic transport is carried out in a carrier medium in the form of a thin layer which is divided into multiple essentially parallel strips.

2. A process according to claim 1 wherein the electrophoretic transport is carried out in a carrier medium which is in the form of a thin layer which is divided into multiple essentially parallel strips which are connected over a narrow stretch near the end opposite to the sample-application end.

3. A process according to claim 1 wherein the strips of the carrier medium for the electrophoretic transport are each held in a channel-shaped compartment, and the substances to be investigated are applied to the respective strips from a section of the respective compartment, which section extends outwardly from the end face of the strip.

4. A process according to claim 1 wherein the carrier medium contains a reagent which promotes precipitation of the substance to be analyzed and/or opposes electroendosmosis.

5. A process according to claim 1 wherein the substances to be investigated are employed in a sample solution which has a different ionic composition and/or ionic concentration from that or those of the aqueous solution in the carrier medium.

* * * * *